(12) United States Patent
Zayas-Rivera et al.

(10) Patent No.: US 7,157,499 B2
(45) Date of Patent: Jan. 2, 2007

(54) MEDICAL APPLICATION OF OXIDIZED MONOTERPENES

(75) Inventors: José Zayas-Rivera, San Juan, PR (US); Naida Montes-Morales, San Juan, PR (US)

(73) Assignee: Zaycor Industries Corp., San Juan, PR (US)

( * ) Notice: Subject to any disclaimer, the term of this patent is extended or adjusted under 35 U.S.C. 154(b) by 695 days.

(21) Appl. No.: 10/016,726

(22) Filed: Oct. 30, 2001

(65) Prior Publication Data

US 2006/0229368 A1   Oct. 12, 2006

(51) Int. Cl.
  *A01N 35/00*     (2006.01)
  *A01N 31/00*     (2006.01)
(52) U.S. Cl. ..................... 514/693; 514/729
(58) Field of Classification Search ............... 514/693, 514/729
  See application file for complete search history.

(56) References Cited

U.S. PATENT DOCUMENTS

| | | | |
|---|---|---|---|
| 5,110,832 A * | 5/1992 | Chastain et al. ............ | 514/729 |
| 5,294,645 A | 3/1994 | Chastain et al. | |
| 5,308,873 A * | 5/1994 | Chastain et al. ............ | 514/729 |
| 5,411,992 A | 5/1995 | Eini et al. | |
| 5,487,988 A * | 1/1996 | Chang et al. ............... | 435/147 |
| 5,763,415 A | 6/1998 | Sukumar | |
| 5,795,566 A * | 8/1998 | Joulain et al. ............. | 424/76.1 |

OTHER PUBLICATIONS

Kurita et al., "Antifungal activity and molecular orbital energies of aldehyde compounds from oils of higher plants", Agricultural and Biological Chemistry (1979), 43(11), pp. 2365-2371 (see enclosed copy of abstract).*

Pamela L. Crowell, Rebekah R. Chang, Zhibin Ren, Charles E. Elson, and Michael N. Gould; Selective Inhibition of Isoprenylation of 21-26-kDa Proteins by the Anticarcinogen d-Limonene and its Metabolites; *The Journal of Biological Chemistry*; 1991; vol. 266, No. 26, pp. 17679, 17681-17685; USA.

Jill D. Haag, Mary J. Lindstrom, and Michael N. Gould; Limonene-induced Regression of Mammary Carcinomas; *Cancer Research*; 1992; pp. 4021-4026; USA.

Bandaru S. Reddy, C-X Wang, Hanan Samaha, Ronald Lubet, Vernone E. Steele, Gary J. Kelloff, and Chinthalapally V. Rae; Chemoprevention of Colon Carcinogenesis by Dietary Perillyl Alcohol; *Cancer Research*; 1997; pp. 420-425; USA.

Gregory H. Ripple, Michael N. Gould, James A. Stewart, Kendra D. Tutsch, Rhoda Z. Arzoomanian, Dona Alberti, Chris Feierabend, Marcia Pomplun, George Wilding, and Howard H. Bailey; Phase I Clinical Trial of Perillyl Alcohol Administered Daily; *Clinical Cancer Research*; 1998; pp. 1159-1164; USA.

Margaret Barthelman, Weixing Chen, Helen L. Gensler, Chuanshu Huang, Zigang Dong, and G. Tim Bowden; Inhibitory Effects of Perillyl ALcohol on UVB-induced Murine Skin Cancer and AP-1 Transactivation; *Cancer Research*; 1998; pp. 711-716; USA.

Piet J. M. Boon, Dennis van der Boon, and Gerard J. Mulder; Cytotoxicity and Biotransformation of the Anticancer Drug Perillyl Alcohol in PC12 Cellsa and in the Rat; Toxicology and Applied Pharmacology; 2000;pp. 55-61; USA.

Gregory H. Ripple, Michael N. Gould, Rhonda Z. Arzoomanian, Dona Alberti, Chris Feierabend, Kim Binger, Kendra D. Tutsch, Marcia Pomplun, Any Wahamaki, Rebecca, Marnocha, George Wilding, and Howard H. Bailey; Phase I Clinical and Pharmacokinetic Study of Perillyl Alcohol Administered Four TImes a Day, *Clinical Cancer Research*; 2000; pp. 390-396; USA.

Gary R. Hudes, Christine E. Szarka, Andrea Adams, Sulabha Ranganathan, Robert A. McCauley, Louis M. Weiner, Corey J. Langer, Samuel Litwin, Gwen Yeslow, Theresa Halberr, Mingxin Qian, and James M. Gallo; Phase I Pharmacokinetic Trial of Perillyl Alcohol (NSC 641066 in Patients with Refractory Solid Malignancies; *Clinical Cancer Research*; 2000; pp. 3071-3080; USA.

Nobuyuki Kurita, Makoto Miyaji, Ryuichiro Kurane, and Yoshimasa Takahara; Antifungal Activity of Componets of Essential Oils; *Agric. Biol. Chem*; 1981; vol. 45, pp. 945-952; USA.

* cited by examiner

*Primary Examiner*—Kevin E. Weddington
(74) *Attorney, Agent, or Firm*—Hoglund & Pamias, PSC; Heath W. Hoglund

(57) ABSTRACT

Preferred compositions used to inhibit the growth of bacteria, fungi and yeast include perillyl aldehyde as an active ingredient. Other active ingredients include perillyl alcohol. The compositions are formed as gels, creams, liquids and dry formulations.

4 Claims, 1 Drawing Sheet

MEDICAL APPLICATION OF OXIDIZED MONOTERPENES

FIELD OF INVENTION

The invention relates generally to the treatment of fungal, bacterial, yeast and other growths.

BACKGROUND OF THE INVENTION

Terpenes are a diverse family of compounds with carbon skeletons composed of five carbon isopentyl (isoprene) units. Terpenes are derived form natural sources such as citrus and pine oils, and are generally considered biodegradable. Common forms of terpenes are d-limonene and α-pinene. Terpenes are classified according to the number of carbon atoms, in units of ten. A terpene with ten carbon atoms is called a monoterpene, one with twenty carbon atoms is a diterpene, and so on.

Various forms of monoterpenes are shown in FIG. 1. These compounds are commercially available. The monterpenes perillyl alcohol (POH) and perillyl aldehyde (PCO) are both derived from the d-limonene structure. POH is formed by the oxidization of carbon number seven (7), i.e., substitution of hydrogen by a hydroxyl group. PCO is formed by the further oxidization of that carbon, i.e., further substitution of hydrogen by another bond to oxygen.

Fungi, bacteria, and yeast, each may be found in a wide variety of species. While some species serve beneficial purposes, others can cause infections, illnesses, and diseases in humans. For example, *Escherichia Coli*, a bacteria, is one of the major causes of urinary tract infections as well as diarrhea, sepsis, and meningitis. *Pseudonoma aeruginosa* is another well-known pathogen that causes infections in wounds and burns. The various species of bacteria respond differently to different treatments.

In medical applications, a treating physician may test for specific bacteria, fungi or yeast. Once identified, the physician may prescribe treatment specific to the microbe causing the illness. Nevertheless, certain treatments do not provide such clinical identification of the microbe. For example, over-the-counter drugs administered without the aid of a physician are generally applied without specific knowledge of the infecting microbe. Such applications require a composition that acts against a wide variety of infections. POH provides relatively effective treatment against bacteria and yeast. Its effectiveness against fungi, however, is limited.

SUMMARY OF THE INVENTION

According to one aspect of the invention a formulation of PCO is suitable to inhibit the growth of bacteria, fungi, yeast and other growths. According to a further aspect of the invention, the formulation of PCO includes SDS as an activity enhancer. According to another aspect of the invention, the formulation of PCO includes POH as another active ingredient.

According to another aspect of the invention a composition is suitable for use as a fungicide and a bacteriacide. The composition includes perillyl aldehyde, and the at least one inactive ingredient. The concentration of perillyl aldehyde is sufficient to inhibit the growth of fungi and bacteria.

According to another aspect of the invention a composition is capable of inhibiting the growth of fungus or a bacteria. The composition includes perillyl aldehyde, and the at least one inactive ingredient. The concentration of the at least one inactive ingredient is greater than the concentration of perillyl aldehyde.

According to another aspect of the invention the growth of bacteria and fungi is inhibited by application of a composition. The composition has an active ingredient and an inactive ingredient. The active ingredient is perillyl aldehyde.

According to another aspect of the invention the growth of fungi or bacteria is inhibited by the application of a composition. The composition includes perillyl aldehyde as an active ingredient and another inactive ingredient. The concentration of the inactive ingredient is greater than the concentration of the active ingredient.

According to another aspect of the invention the growth of microbes infecting a host is inhibited by application of PCO and POH in a concentration of the at least 0.5% PCO.

According to another aspect of the invention the growth of bacteria or fungi infecting a host is inhibited by application of PCO and SDS.

Further aspects of the invention will be appreciated with reference to the drawings and detailed description.

DETAILED DESCRIPTION

Figure 1:
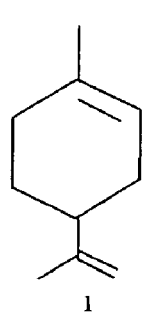
FIG. 1 is a diagram showing various forms of monoterpenes, which are commercially available.
Figure 1:
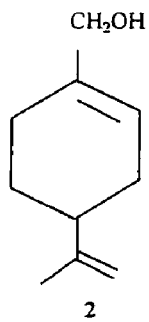
Figure 1:
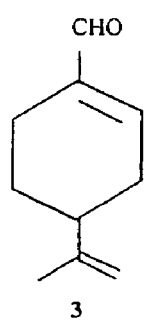
Figure 1:
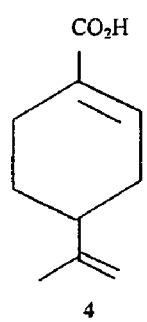
Figure 1:
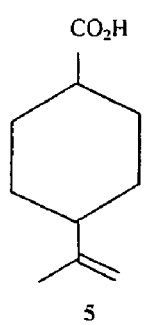
Figure 1:
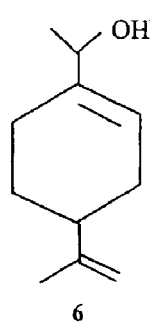
Figure 1:
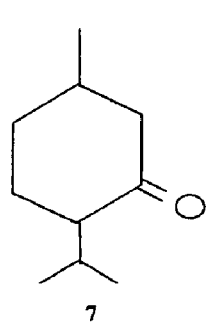
Figure 1:
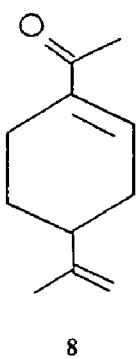
Figure 1:
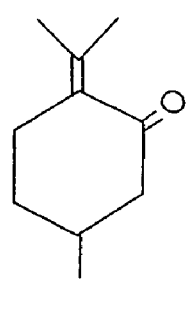
Figure 1:
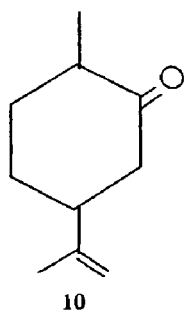
Figure 1:
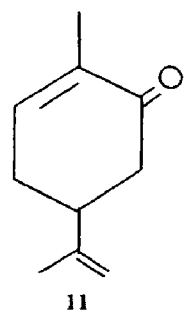

According to preferred embodiments of the invention (1) PCO, and (2) PCO and POH are formulated for the treatment of bacteria, fungi, yeast, and other growths. Preferred formulations show effective inhibition of the growth of bacteria, fungi and yeast.

The formulations prepared using (1) PCO, and (2) PCO and POH demonstrated anti-bacterial activity with the agar diffusion-disk technique. This technique is explained in R. K. Dart, Microbiology for the Analytic Chemist, The Royal Society of Chemists, 1996, which is incorporated herein by reference. Plating seven (7) different bacterial strains, shows the response to the formulations including either PCO or POH or both. Anti-bacterial activity was detected by showing a distinguished halo around the disk previously wetted with the formulation. Halo formation was measured with a caliper and biological activity was considered according to size. Details of specific applications and formulations are set forth below. The following Table 0.1 summarizes various results:

TABLE 0.1

| | BACTERIAL STRAINS | | | | | | |
|---|---|---|---|---|---|---|---|
| Formulation | E. coli | Ps. aeruginosa | B. cepacea | S. typhim | S. aureus | S. epiderm | B. subtilis |
| Control Water | nh | nh | nh | nh | nh | nh | nh |
| 1% SDS | nh | nh | nh | nh | nh | nh | nh |

TABLE 0.1-continued

| | BACTERIAL STRAINS | | | | | | |
|---|---|---|---|---|---|---|---|
| Formulation | E. coli | Ps. aeruginosa | B. cepacea | S. typhim | S. aureus | S. epiderm | B. subtilis |
| 1% PCO, 0.1% SDS | 0.52 | 2.06 | 0.66 | 0.21 | 0.16 | 0.27 | 4.19 |
| 2% PCO | 0.75 | 4.81 | 0.8 | nm− | 0.86 | 0.52 | nm+ |
| 1% PCO, 1% POH | 1.45 | 5.59 | 0.7 | 0.92 | 0.79 | 0.2 | 5.66 |
| 1% POH, 0.1% SDS | 0.34 | 4.1 | 0.63 | 0.37 | 1.09 | nm− | 4.03 |

In the above table, nh indicates no-halo; n/a indicates not applicable; nm− indicates not measurable due to small halo; nm+ indicates not measurable due to total inhibition. SDS indicates Sodium Dodecyl Sulfate.

The most sensitive bacterial strain was *B. subtilis*, which showed a broad halo, providing almost total inhibition of growth.

The 1% PCO formulation produces an immediate decrease in bacterial and yeast concentration. This response is stronger than that observed for POH. The 0.5% PCO/0.5% POH formulation also produces an immediate decrease in bacterial and yeast concentration. This response is stronger than that observed for either PCO or POH in the same concentration.

Although SDS or propylene glycol generally do not provide activity against bacterial cells, they do enhance the inhibition provided by PCO and POH, each alone or in combination. Nonetheless the use of 0.1% SDS was enough to kill *S. aureus*.

In addition, disinfectant formulations with propylene glycol or polyethylene glycol (PEG 400) show parallel results, these compounds act as an enhancer and help to keep the PCO and/or POH in solution. These enhancers, however, generally have no effect against bacteria, yeast or fungi. Only the primary action of PCO and/or POH was observed.

In addition, the growth of yeast and fungi (specifically *C. albicans* and *A. niger*) are also inhibited by PCO. Details of specific applications and formulations are set forth below. The following Table 0.2 summarizes the results.

TABLE 0.2

| | FUNGAL STRAINS | |
|---|---|---|
| Formulation | C. albicans | A. niger |
| Control Water | nh | nh |
| 1% SDS | nh | nh |
| 1% PCO, 0.1% SDS | 6.73 | 3.83 |
| 2% PCO | nm+ | n/a |
| 1% PCO, 1% POH | 4.6 | n/a |
| 1% POH, 0.1% SDS | 0.93 | 2.19 |

The inhibition power of the formulations with PCO is more effective than with POH for these two organisms. The effect of PCO formulation lasts longer in fungi and yeast than the effect of POH formulation. Specifically, 96 hours after inhibition there was re-growth around the POH formulation, whereas there is no growth around the PCO formulation in *A. niger*. Further experiments have shown that the formulation using PCO at 0.5% is very active against *A. niger* even after 7 days, whereas considerable growth was observed for the same experiment using the same concentration of POH.

Formulations were further tested against a culture of the fungi *A. niger*. The fungi was exposed to 1% PCO/1% POH, 1% PCO, and 1% POH formulations. All formulations were prepared in a glycerol/SDS base in water. In this test, after 18 hours of exposure the 1% PCO/1% POH formulation killed the fungi where it was placed and limited the growth over a 2.44 mm halo around the disk moistened with the formulation. The formulations of 1% PCO and 1% POH did not show a measurable halo but did inhibit the growth in the area where it was placed. Furthermore, after 12 days of continued incubation the 1% PCO/1% POH showed no growth in the halo and appears to have a limited growth at the edge of the halo. Moreover, no growth was observed at the top of the disk and no growth beneath the disk. Also no growth was observed in the disk top of the other two formulations. Under more controlled conditions a 0.5 and 1% formulations of PCO did inhibit growth of *A. niger*, whereas POH did not perform as aggressively.

Moreover, *C. albicans* was cultured in Sabouraud-Dextrose media and was exposed to a cream formulation having 0.75% perillaldehyde. A well was made in the middle of the agar and filled with the 0.75% perillaldehyde cream. After 24 hours, the distinguished halo appeared as soon as the diffusion of active ingredient (PCO) passes across the agar.

The following examples illustrate the antibacterial and antifungal properties of various formulations. The formulations are applied to common bacterial fungal and yeast strains.

EXAMPLE 1

*E. coli*

Again, *E. coli* is one of the major causes of urinary tract infections as well as diarrhea, sepsis and meningitis. The formulations were exposed against cultures of *E. coli* showing growth inhibition.

About $1-2 \times 10^6$ cells of *E. coli* were exposed to 1% PCO, 1% PCO/1% POH, 1% POH and 0.5% PCO/0.5% POH formulations at 10, 30, and 60 minutes. Once the bacteria were exposed to formulations in the determined time, a 0.5 ml aliquot of exposition mix was used to inoculate 10 ml of TSB media and incubated at 35° C. for 18–24 hours. Absorbance (Abs.) measures were taken at 600 nm. After 10 minutes of exposure the bacterial growth was inhibited.

The following tables 1.1, 1.2, 1.3, and 1.4, show the responses for 1% PCO, 1% PCO/1% POH, 1% POH and 0.5% PCO/0.5% POH formulations, respectively.

TABLE 1.1

1% PCO Formulation

| Exposure time | E. coli Abs. 600 nm |
|---|---|
| 0 minutes | 0.8912 |
| 10 minutes | 0.0032 |
| 30 minutes | 0.0033 |
| 60 minutes | 0.0019 |

TABLE 1.2

1% PCO/1% POH Formulation

| Exposure time | E. coli Abs. 600 nm |
|---|---|
| 0 minutes | 0.9254 |
| 10 minutes | 0.0217 |
| 30 minutes | 0.0126 |
| 60 minutes | 0.0609 |

TABLE 1.3

1% POH Formulation

| Exposure time | E. coli Abs. 600 nm |
|---|---|
| O minutes | 0.8727 |
| 10 minutes | 0.0057 |
| 30 minutes | 0.0050 |
| 60 minutes | 0.0067 |

TABLE 1.4

0.5% PCO 0.5% POH Formulation

| Exposure time | E. coli Abs. 600 nm |
|---|---|
| O minutes | 0.8628 |
| 10 minutes | 0.1031 |
| 30 minutes | 0.1017 |
| 60 minutes | 0.0812 |

TABLE 2.1

1% PCO Formulation

| Exposure time | Ps. Aeruginosa Abs. 600 nm |
|---|---|
| Control | 0.2582 |
| 10 minutes | 0.0039 |
| 30 minutes | 0.0004 |
| 60 minutes | 0.0050 |

TABLE 2.2

1% PCO/1% POH Formulation

| Exposure time | P. aeruginosa Abs. 600 nm |
|---|---|
| Control | 0.7948 |
| 10 minutes | 0.0215 |
| 30 minutes | 0.0142 |
| 60 minutes | 0.0429 |

TABLE 2.3

1% POH Formulation

| Exposure time | P. aeruginosa Abs. 600 nm |
|---|---|
| Control | 0.2089 |
| 10 minutes | 0.0129 |
| 30 minutes | 0.0200 |
| 60 minutes | 0.0262 |

TABLE 2.4

Ps. aeruginosa 0.5% PCO/0.5% POH Formulation

| Exposure time | P. aeruginosa Abs. 600 nm |
|---|---|
| Control | 0.2089 |
| 10 minutes | 0.0129 |
| 30 minutes | 0.0200 |
| 60 minutes | 0.0262 |

EXAMPLE 2

*Pseudomona aeruginosa*

*Pseudonoma aeruginosa* (*P. aeruginosa*) is a well known pathogen which is the cause of infections in wounds and burns. It also causes meningitis and urinary tract infections. If it invades the bloodstream system, it may result in fatal sepsis, and skin infections causing necrosis and ecthyma gangrenosum.

About $1-2 \times 10^6$ cells of *P. aeruginosa* were exposed to 1% PCO, 1% PCO/1% POH, 1% POH and 0.5% PCO/0.5% POH formulation at 10, 30, and 60 minutes. Once the bacteria were exposed to formulation in the determined time, a 0.5 ml aliquot of exposition mix was used to inoculate 10 ml of TSB media and incubated at 35° C. for 18–24 hours. Absorbance measures were taken at 600 nm. After 10 minutes of exposure the bacterial growth was inhibited.

The following Tables 2.1, 2.2, 2.3, and 2.4, show the responses for 1% PCO, 1% PCO/1% POH, 1% POH, and 0.5% PCO/0.5% POH formulations, respectively.

EXAMPLE 3

*Burkholderia cepacea*

*Burkholderia cepacea* (*B. cepacea*) is found in patients with cystic fibrosis, and other pulmonary infections.

About $1-2 \times 10^6$ cells of *B. cepacea* were exposed to 1% PCO, 1% POH 1% PCO/1% POH, and 0.5% PCO/0.5% POH formulations at 10, 30, and 60 minutes. Once the bacteria were exposed to formulation in the determined time, a 0.5 ml aliquot of exposition mix was used to inoculate 10 ml of TSB media and incubated at 35° C. for 18–24 hours. Absorbance measures were taken at 600 nm. After 10 minutes of exposure the bacterial growth was inhibited. *B. cepacea* exhibited a low growth of control cells. Nonetheless, the diminishing in the absorbance values and the lack of turbidity in the broth culture shows growth inhibition.

The following tables 3.1, 3.2, 3.3, and 3.4, show the responses for 1% PCO, 1% POH, 1% PCO/1% POH, and 0.5% PCO/0.5% POH, respectively.

TABLE 3.1

1% PCO Formulation

| Exposure time | B. cepacea abs. 600 nm |
|---|---|
| Control | 0.1533 |
| 10 minutes | 0.0110 |
| 30 minutes | 0.0076 |
| 60 minutes | 0.0072 |

TABLE 3.2

1% POH Formulation

| Exposure time | B. cepacea abs. 600 nm |
|---|---|
| Control | 0.0286 |
| 10 minutes | 0.0107 |
| 30 minutes | 0.0079 |
| 60 minutes | 0.0101 |

TABLE 3.3

1% PCO 1% POH Formulation

| Exposure time | B. cepacea absorbance 600 nm |
|---|---|
| Control | 0.1533 |
| 10 minutes | 0.0686 |
| 30 minutes | 0.0427 |
| 60 minutes | 0.0645 |

TABLE 3.4

0.5% PCO 0.5% POH Formulation

| Exposure time | B. cepacea abs. 600 nm |
|---|---|
| Control | 0.1533 |
| 10 minutes | 0.075 |
| 30 minutes | 0.0355 |
| 60 minutes | 0.0557 |

TABLE 4.1

1% POC Formulation

| Exposure time | S. typhimurum abs. 600 nm |
|---|---|
| Control | 0.8172 |
| 10 minutes | 0.0053 |
| 30 minutes | 0.0053 |
| 60 minutes | 0.0052 |

TABLE 4.2

1% POH Formulation

| Exposure time | S. typhimurum abs. 600 nm |
|---|---|
| Control | 0.8577 |
| 10 minutes | 0.0237 |
| 30 minutes | 0.0228 |
| 60 minutes | 0.0130 |

TABLE 4.3

1% POH/1% PCO Formulation

| Exposure time | S. typhimurum abs. 600 nm |
|---|---|
| Control | 0.3128 |
| 10 minutes | 0.0187 |
| 30 minutes | 0.0138 |
| 60 minutes | 0.0695 |

TABLE 4.4

0.5% PCO, 0.5% POH Formulation

| Exposure time | S. typhimurum abs. 600 nm |
|---|---|
| Control | 0.9274 |
| 10 minutes | 0.1064 |
| 30 minutes | 0.1231 |
| 60 minutes | 0.0926 |

EXAMPLE 4

*Salmonella typhimurum*

*Salmonella Typhimurum* (*S. typhimurum*) causes typhoid fever or enteric fever and gastroenteritis or enterocolotis. Typhoid fever symptoms are headache, enlargement of the liver and spleen, and rose spots. Other lesions are hyperplasia and necrosis of lymphoid tissue.

About $1–2\times10^6$ cells of *S. typhimurum* were exposed to 1% PCO, 1% POH 1% PCO/1% POH, and 0.5% PCO/0.5% POH formulations at 10, 30, and 60 minutes. Once the bacteria were exposed to formulation in the determined time, a 0.5 ml aliquot of exposition mix was used to inoculate 10 ml of TSB media and incubated at 35° C. for 18–24 hours. Absorbance measures were taken at 600 nm. After 10 minutes of exposure, the bacterial growth was inhibited.

The following tables 4.1, 4.2, 4.3, and 4.4, show the responses for 1% POC, 1% POH, 1% PCO/1% POH, and 0.5% PCO/0.5% POH formulations, respectively.

EXAMPLE 5

*Staphylococcus aureus*

*Staphylococcus aureus* (*S. aureus*) causes Toxic Shock Syndrome, and also causes wound skin infections, bacteremia, endocarditis (caused by contaminated medical devices), meningitis, hematogenous osteomyelitis, or pulmonary infections. Bacteremia is particularly hard to cure because it develops resistance to antibiotics.

About $1–2\times10^6$ cells of *S. aureus* were exposed to 1% PCO, 1% POH 1% PCO/1% POH, 0.5% PCO/0.5% POH, 0.5% PCO/0.006% SDS, and 0.25% PCO/0.003% SDS formulations at 10, 30, and 60 minutes. Once the bacteria were exposed to formulation in the determined time, a 0.5 ml aliquot of exposition mix was used to inoculate 10 ml of TSB media and incubated at 35° C. for 18–24 hours. Absorbance measures were taken at 600 nm. In addition, *S. aureus* was susceptible to 0.1% SDS in positive control. Lowering the percentage of SDS (to 0.003% SDS) showed growth in the positive controls. After ten minutes in terpene (mixture of PCO and POH) exposure in formulation low in SDS, the bacterial growth was inhibited.

The following Tables 5.1, 5.2, 5.3, 5.4, 5.5, and 5.6, show the responses for 1% PCO, 1% POH, 1% PCO/1% POH, 0.5% PCO/0.006% SDS, and 0.25% PCO/0.003% SDS, respectively.

TABLE 5.1

1% PCO Formulation

| Exposure time | S. aureus abs. 600 nm |
|---|---|
| Control | 0.9945 |
| 10 minutes | 0.0422 |
| 30 minutes | 0.0464 |
| 60 minutes | 0.0426 |

TABLE 5.2

1% POH Formulation

| Exposure time | S. aureus abs. 600 nm |
|---|---|
| Control | 0.9945 |
| 10 minutes | 0.0135 |
| 30 minutes | 0.0183 |
| 60 minutes | 0.0111 |

TABLE 5.3

1% PCO/1% POH Formulation

| Exposure time | S. aureus abs. 600 nm |
|---|---|
| Control | 0.9945 |
| 10 minutes | 0.0200 |
| 30 minutes | 0.0210 |
| 60 minutes | 0.0218 |

TABLE 5.4

1% Terpene Formulation (0.5% PCO/0.5% POH)

| Exposure time | S. aureus absorbance at 600 nm |
|---|---|
| Control | 0.8376 |
| 10 minutes | −0.0103 |
| 30 minutes | −0.007 |
| 60 minutes | −0.0027 |

TABLE 5.5

0.5% PCO, 0.006% SDS Formulation

| Exposure time | S. aureus absorbance at 600 nm |
|---|---|
| Control | 0.8376 |
| 10 minutes | −0.0029 |
| 30 minutes | −0.0062 |
| 60 minutes | −0.0021 |

TABLE 5.6

0.25% PCO, 0.003% SDS Formulation

| Exposure time | S. aureus abs. 600 nm |
|---|---|
| Control | 0.8376 |
| 10 minutes | 0.0237 |
| 30 minutes | 0.0178 |
| 60 minutes | 0.0186 |

EXAMPLE 6

*Staphylococcus epidermidis*

*Staphylococcus epidermidis* (*S. epidermidis*) are part of the normal human flora of the skin and respiratory and gastrointestinal tracts. Nonetheless *S. epidermidis* can cause infection and become resistant to antibiotics.

About $1–2\times10^6$ cells of *S. epidermidis* were exposed to 1% PCO, 1% POH, 1% PCO/1% POH, and 0.5% PCO/0.5% POH formulations at 10, 30, and 60 minutes. Once the bacteria were exposed to formulation in the determined time, a 0.5 ml aliquot of exposition mix was used to inoculate 10 ml of TSB media and incubated at 35° C. for 18–24 hours. Absorbance measures were taken at 600 nm. After 10 minutes of exposure, the bacterial growth was inhibited.

The following Tables 6.1, 6.2, 6.3, and 6.4, show the responses for 1% PCO, 1% POH, 1% PCO/1% POH, and 0.5% PCO/0.5% POH Formulations, respectively.

TABLE 6.1

1% PCO Formulation

| Exposure time | S. epidermidis abs. 600 nm |
|---|---|
| Control | 0.3153 |
| 10 minutes | 0.0418 |
| 30 minutes | 0.0448 |
| 60 minutes | 0.0394 |

TABLE 6.2

1% POH Formulation

| Exposure time | S. epidermidis abs. 600 nm |
|---|---|
| Control | 0.3153 |
| 10 minutes | 0.0119 |
| 30 minutes | 0.0136 |
| 60 minutes | 0.0162 |

TABLE 6.3

1% PCO/1% POH Formulation

| Exposure time | S. epidermidis abs. 600 nm |
|---|---|
| Control | 0.3153 |
| 10 minutes | 0.0283 |
| 30 minutes | 0.0232 |
| 60 minutes | 0.0210 |

TABLE 6.4

0.5% PCO, 0.5% POH Formulation

| Exposure time | S. epidermidis abs. 600 nm |
|---|---|
| Control | 0.1764 |
| 10 minutes | 0.0447 |
| 30 minutes | 0.0111 |
| 60 minutes | 0.0006 |

EXAMPLE 7

Bacillus subtilis

*Bacillus subtilis* (*B. subtilis*) is not a normal flora member, but is not a pathogen either. It is produced by spores, and is one of the control organism used in autoclave effectiveness.

About $1–2\times10^6$ cells of *B. subtilis* were exposed to 1% PCO, 1% POH, 1% PCO/1% POH and 0.5% PCO/0.5% POH formulations at 10, 30, and 60 minutes. Once the bacteria were exposed to formulation in the determined time, a 0.5 ml aliquot of exposition mix was used to inoculate 10 ml of TSB media and incubated at 35° C. for 18–24 hours. Absorbance measures were taken at 600 nm. After 10 minutes of exposure the bacterial growth was inhibited.

The following Tables 7.1, 7.2, 7.3, and 7.4, show the responses to 1% PCO, 1% POH, 1% PCO/1% POH and 0.5% PCO/0.5% POH formulations, respectively.

TABLE 7.1

1% PCO Formulation

| Exposure time | *B. subtilis* abs. 600 nm |
|---|---|
| Control | 0.9077 |
| 10 minutes | 0.0006 |
| 30 minutes | −0.0058 |
| 60 minutes | −0.0113 |

TABLE 7.2

1% POH Formulation 1%

| Exposure time | *B. subtilis* abs. 600 nm |
|---|---|
| Control | 0.9077 |
| 10 minutes | 0.0248 |
| 30 minutes | 0.0269 |
| 60 minutes | 0.0463 |

TABLE 7.3

1% PCO/1% POH Formulation

| Exposure time | *B. subtilis* abs. 600 nm |
|---|---|
| Control | 0.9077 |
| 10 minutes | 0.0165 |
| 30 minutes | 0.0300 |
| 60 minutes | 0.0205 |

TABLE 7.4

0.5% PCO, 0.5% POH Formulation

| Exposure time | *B. subtilis* abs. 600 nm |
|---|---|
| Control | 1.1278 |
| 10 minutes | 0.0351 |
| 30 minutes | 0.0616 |
| 60 minutes | 0.0570 |

EXAMPLE 8

Candida albicans

*Candida albicans* (*C. albicans*) causes vulvovaginal infections. Usually irritation, pruritus, and vaginal discharge are present. This is often lead by factors such as diabetes, pregnancy and some antibacterial drugs that alter the normal flora.

About $1–2\times10^6$ cells of *C. albicans* were exposed to 1% PCO, 1% POH, 1% PCO/1% POH, and 0.5% PCO/0.5% POH, formulations at 10, 30, and 60 minutes. Once the fungi were exposed to formulation in the determined time, a 0.5 ml aliquot of exposition mix was used to inoculate 10 ml of TSB media and incubated at 35° C. for 18–24 hours. Absorbance measures were taken at 600 nm. After 10 minutes of exposure, the fungal growth was inhibited.

The following Tables 8.1, 8.2, 8.3, 8.4, show the responses to 1% PCO, 1% POH, 1% PCO/1% POH, and 0.5% PCO/0.5% POH formulations, respectively.

TABLE 8.1

1% PCO Formulation

| Exposure time | *C. albicans* abs. 600 nm |
|---|---|
| Control | 0.4093 |
| 10 minutes | 0.0050 |
| 30 minutes | 0.0070 |
| 60 minutes | 0.0054 |

TABLE 8.2

1% POH Formulation

| Exposure time | *C. albicans* abs. 600 nm |
|---|---|
| Control | 0.4093 |
| 10 minutes | 0.0529 |
| 30 minutes | 0.0332 |
| 60 minutes | 0.0449 |

TABLE 8.3

1% PCO/1% POH Formulation

| Exposure time | *C. albicans* abs. 600 nm |
|---|---|
| Control | 0.4093 |
| 10 minutes | 0.0083 |
| 30 minutes | 0.0240 |
| 60 minutes | 0.0225 |

TABLE 8.4

0.5% PCO/0.5% POH Formulation

| Exposure time | *C. albicans* abs. 600 nm |
|---|---|
| Control | 0.2067 |
| 10 minutes | 0.0350 |
| 30 minutes | 0.0227 |
| 60 minutes | 0.0350 |

EXAMPLE 9

Aspergillus niger

*Aspergillus niger* (*A. niger*) causes aspergillosis, especially in immunosuppressive patients. Non-invasive infections may involve the ear canal, cornea or the nails. In invasive aspergillosis the symptoms may include fever, cough, dyspnea, hemoptysis, or may cause thrombosis, infarction and necrosis.

About $1\times10^6$ cells of *Aspergillus niger* were exposed to 1% PCO, 1% POH and 0.5% PCO/0.5% POH formulations at 10, 30, and 60 minutes. Once the bacteria were exposed to formulation in the determined time, a 0.5 ml aliquot of exposition mix was used to inoculate 10 ml of TSB media and incubated at 35° C. for 48 hours. Absorbance measures were taken at 600 nm. After 10 minutes of exposure, the fungal growth was inhibited.

The following Tables 9.1, 9.2, and 9.3, show the responses to 1% PCO, 1% POH and 1% Terpene (0.5% PCO/0.5% POH) formulations, respectively.

TABLE 9.1

1% PCO Formulation

| Exposure time | *A. niger* Abs. 600 nm |
|---|---|
| Control | 0.4394 |
| 10 minutes | 0.0137 |
| 30 minutes | 0.0149 |
| 60 minutes | 0.0163 |

TABLE 9.2

1% POH Formulation

| Exposure time | *A. niger* Abs. 600 nm |
|---|---|
| Control | 0.4394 |
| 10 minutes | 0.0316 |
| 30 minutes | 0.0204 |
| 60 minutes | 0.0092 |

TABLE 9.3

1% Terpene (0.5% PCO/0.5% POH) Formulation

| Exposure time | *A. niger* Abs. 600 nm |
|---|---|
| Control | 0.4394 |
| 10 minutes | 0.0411 |
| 30 minutes | 0.0459 |
| 60 minutes | 0.0326 |

Turning now to preferred formulations, a cream, an ointment, a gel, and a dry and wet formulation are described.

A preferred cream formulation includes PCO as an active ingredient, and octadecanol, propanediol, hexadecanol, oleic acid, and mineral oil, as inactive ingredients. The cream formulation acts as a bactericide, fungicide and disinfectant. The cream formulation is suitable to treat infections such as skin (pruritus) or vaginal candidiasis, skin wounds, and burns. It is also suitable to treat against nail or ear aspergillosis and other skin fungi.

TABLE 10.1 below lists the specific composition of a preferred 1% PCO formulation.

| Order | Reagent | Amount ml | Amount | % |
|---|---|---|---|---|
| 1 | Octadecanol | — | 1.0 g | 14.091 |
| 2 | Propanediol | 5 ml | 5.18 g | 72.994 |
| 3 | Hexadecanol | — | 0.8 g | 11.273 |
| 4 | Oleic acid | 0.025 ml | 0.022275 g | 0.314 |
| 5 | Mineral oil | 0.025 ml | 0.021875 g | 0.308 |
| 6 | PCO | 0.075 ml | 0.0723375 g | 1.019 |
| | Total | | 7.0964875 g | 100.00% |

TABLE 10.2 below lists the specific composition of a 0.76% PCO formulation.

| Order | Reagent | Amount ml | Amount | % |
|---|---|---|---|---|
| 1 | Octadecanol | — | 1.0 g | 10.5 |
| 2 | Hexadecanol | — | 0.8 g | 8.4 |
| 3 | Propanediol | 7.0 ml | 7.252 g | 76.16 |
| 4 | Oleic acid | 0.025 ml | 0.022275 g | 0.23 |
| 5 | Mineral oil | 0.200 ml | 0.175 g | 1.84 |
| 6 | DI Water | 0.200 ml | 0.2 g | 2.1 |
| 7 | PCO | 0.075 ml | 0.072338 g | 0.76 |
| | Total | | 9.521613 | 100.00% |

A preferred ointment formulation includes PCO as an active ingredient and bees wax, mineral oil, and hexadecanol, as inactive ingredients. The ointment formulation is suitable to treat infections such as skin (pruritus) or vaginal candidiasis, skin wounds and burns, against nail or ear aspergillosis and other skin fungi.

TABLE 11.1 below lists the specific composition of a preferred 1% PCO ointment.

| Order | Reagent | Amount ml | Amount | % |
|---|---|---|---|---|
| 1 | Bees Wax | — | 1.2 g | 11.68 |
| 2 | Mineral Oil | 10 ml | 8.75 g | 85.179 |
| 3 | Hexadecanol | — | 0.2 g | 1.947 |
| 4 | PCO | 0.127 ml | 0.1225 g | 1.193 |
| | Total | | 7.0964875 g | 100.00% |

A preferred gel includes PCO as an active ingredient, and hydroxypropyl cellulose, Tween 60, DI water, carbopol 940, sodium bicarbonate and isopropanol 70% as inactive ingredients. The gel formulation is suitable to treat infections such as skin (pruritus) or vaginal candidiasis, skin wounds and to prevent burn infections, against nail or ear aspergillosis and other skin fungi.

TABLE 12.1 below lists the specific composition of one preferred gel formulation.
Gel Formulation - No PCO

| Order | Reagent | Amount ml | Amount | % |
|---|---|---|---|---|
| 1 | Hydroxypropyl cellulose | — | 0.6 g | 0.545 |
| 2 | Tween 60 | — | 4.0 g | 3.635 |
| 3 | DI Water | 100.0 ml | 100.0 g | 90.884 |
| 4 | Carbopol 940 | — | 1.0 g | 0.908 |
| 5 | Sodium Bicarbonate | — | 0.5 g | 0.454 |
| 6 | Isopropanol 70% | 5.0 ml | 3.93 g | 3.572 |
| | Total | | 110.03 g | 99.998% |

25 g of Gel Formulation were used and 0.1206 g of PCO was added for a 0.5% PCO gel. Table 12.2 below lists the specific composition of one preferred 0.5% PCO gel formulation.

| Order | Reagent | Amount g | % |
|---|---|---|---|
| 1 | Hydroxypropyl cellulose | 0.1363 g | 0.543 |
| 2 | Tween 60 | 0.9088 | 3.618 |
| 3 | DI Water | 22.7211 | 90.448 |

-continued

| Order | Reagent | Amount g | % |
|---|---|---|---|
| 4 | Carbopol 940 | 0.2272 | 0.904 |
| 5 | Sodium Bicarbonate | 0.1136 | 0.452 |
| 6 | Isopropanol 70% | 0.8929 | 3.554 |
| 7 | Perillyl aldhyde | 0.1206 g | 0.480 |
| | Total | 25.1205 | 99.999 |

A preferred dry formulation includes PCO as an active ingredient and SDS as an enhancer. The dry formulation is suitable to be packed in pouches such as Hydrolene® material for household, pharmaceutical or hospital critical cleaning and disinfection, and germ-free prosthetic devices by dilution directly into water. This avoids bulky bottles for packaging and allows shipment of low weight pouches instead of, for example, one-gallon bottles.

One preferred formulation having 22.5% PCO stock includes 1 ml PCO (90%), 1 ml 2.5% SDS in propylene glycol, and 2 ml propylene glycol (or polyethylene glycol).

Another preferred formulation having 21.25% POH stock includes 1 ml POH 85%, 1 ml 10% SDS in propylene glycol, and 2 ml propylene glycol.

Another preferred formulation having 11.9% PCO and 11.9% POH includes 0.55 ml PCO (90%), 0.58 ml POH, 1 ml 10% SDS in propylene glycol, and 2 ml propylene glycol (or polyethylene glycol).

Preferred Wet Formulations are suitable for household, pharmaceutical or hospital critical cleaning and disinfection limiting the propagation of gastroenteritis, enterocolitis, pneumonia, and other nosocomials diseases. In addition, these formulations are useful for disinfections of prosthetic devices, surgical clothes disinfection, or in wastewater treatment plants, as well as in meat or poultry food manufacturing plants. These formulations are also suitable in atomizer bottle sprays over bookshelves against books mold and fungi.

One preferred formulation having a 1% PCO solution includes 1 ml PCO stock, and 21.5 ml deionized ultra filtered water.

Another preferred formulation having a 1% POH solution includes 1 ml of POH stock, and 20.25 ml of deionized ultra filtered water.

Yet another preferred formulation having a 1% terpene solution includes 1 ml of terpene stock, and 22.8 ml of deionized ultra filtered water.

Yet another preferred formulation having a 50% terpene solution includes 1.11 ml of 90% PCO, 1.17 ml of 85% POH, 1 ml of 10% SDS in propylene glycol, and 2 ml of propylene glycol.

Yet another preferred formulation having a 2% terpene solution includes 1 ml of 50% Terpene stock, 24 ml of deionized ultra filtered water.

Although the invention has been described with reference to specific preferred applications and formulations, those skilled in the art will appreciate that many modifications and variations to such applications and formulations may be made without departing from the teachings of the invention. All such modifications and variations are intended to be encompassed within the scope of the following claims.

We claim:

1. A method of inhibiting the growth of *E. coli, P. aeruginosa, B. cepacea, S. typhimurum, S. aureus, S. epidermidis, B. subtilis, A. niger*, and *C. albicans* comprising the step of applying a composition containing perillyl aldehyde in a concentration of 1 percent by weight.

2. A method of inhibiting the growth of fungi or a bacteria comprising the step of applying a composition containing perillyl aldehyde, wherein a concentration of 1 percent by weight of perillyl aldehyde is sufficient to inhibit the growth of *E. coli, P. aeruginosa, B. cepacea, S. typhimurum, S. aureus, S. epidermidis, B. subtilis, A. niger* and *C. albicans*.

3. A method of inhibiting the growth of a bacteria comprising the step of applying a composition containing perillyl aldehyde, wherein a concentration of 1 percent by weight perillyl aldehyde is sufficient to inhibit the growth of *E. coli, P. aeruginosa, B. cepacea, S. typhimurum, S. aureus, S. epidermidis, B. subtilis*.

4. A method of inhibiting the growth of *E. coli, P. aeruginosa, B. cepacea, S. aureus, S. epidermidis, B. subtilis* comprising the step of applying a composition containing perillyl aldehyde in a concentration of 1 percent by weight.

* * * * *